United States Patent [19]

Fekete et al.

[11] Patent Number: 5,726,201

[45] Date of Patent: Mar. 10, 1998

[54] GEMFIBROZIL CONTAINING PHARMACEUTICAL COMPOSITIONS

[75] Inventors: Pál Fekete; Erzsébet Fellner, née Kóhalmi; Andrea Sándorfalvy; Dénes Bezzegh; György Ujfalussy; Magdolna Góra, née Hernyes; Imre Klebovich; Sándor Drabant; Attila Mándi; Bíborka Maroshelyi, née Kovács; Márta Szántó ; Zsuzsa Szlávy, née Széll, all of Budapest, Hungary

[73] Assignee: Egis Gyogyszergyar Rt., Budapest, Hungary

[21] Appl. No.: 441,687

[22] Filed: May 15, 1995

[51] Int. Cl.$^6$ .................................................. A61K 31/34
[52] U.S. Cl. ..................... 514/471; 514/568; 424/465; 424/476
[58] Field of Search .......................... 514/568, 471; 424/465, 476

[56] References Cited

U.S. PATENT DOCUMENTS

| | | | |
|---|---|---|---|
| 3,674,836 | 7/1972 | Creger | 260/473 G |
| 4,126,637 | 11/1978 | Goel et al. | 562/421 |
| 4,925,676 | 5/1990 | Ghebre-Sellassie et al. | 424/465 |
| 4,927,639 | 5/1990 | Ghebre-Sellassie et al. | 424/497 |
| 4,971,804 | 11/1990 | Ghebre-Sellassie et al. | 424/490 |
| 5,281,421 | 1/1994 | Ghebre-Sellassie et al. | 424/465 |

*Primary Examiner*—Brian M. Burn
*Attorney, Agent, or Firm*—Beveridge, DeGrandi, Weilacher & Young, L.L.P.

[57] ABSTRACT

The invention relates to oral solid pharmaceutical composition containing as active ingredient gemfibrozil and conventional pharmaceutical auxiliary agents comprising as surfactant bis-(2-ethyl-hexyl)-sodium-sulfosuccinate in an amount of 0.05–0.5% by weight relative to gemfibrozil content of the composition.

The pharmaceutical compositions according to the present invention contain a relatively small amount of a surfactant, provide uniform dissolution of the active ingredient among the different batches and the standard deviation of the dissolution rate is low.

20 Claims, 6 Drawing Sheets

GEMFIBROZIL CONTAINING PHARMACEUTICAL COMPOSITIONS

According to the present invention there are provided oral solid gemfibrozil containing pharmaceutical compositions and a process for the preparation thereof. More particularly the invention relates to oral gemfibrozil compositions, preferably in the form of tablets, film-coated tablets and capsules.

Gemfibrozil—5-(2,5-dimethylphenoxy)-2,2-dimethylpentanoic acid—is a widely used antihyperlipoproteinemic agent having a high daily dose ranging between 900 mg and 1500 mg. The active agent is poorly water soluble and has a hydrophobic character. For this reason the preparation of gemfibrozil containing pharmaceutical compositions with adequate dissolution and adsorption of the active ingredient involves serious difficulties.

In the commercially available compositions various surfactants are used to promote the dissolution of the active ingredient. Thus the 300 mg capsule and 600 mg tablet marketed in the USA (manufacturer: Parke Davis) contains as surfactant polysorbate 80 [mono-9-octadecanoate poly (oxy-1,2-ethanediyl)-sorbitane derivative] and sodium lauryl sulfate, respectively [Physicians Desk Reference, 45th Edition, (1991), publisher: E. R. Barnhart, Oradell, N.Y. USA, page 1668]. The 450 mg gemfibrozil containing tablet put on the market in Germany by Parke Davis also comprises a polysorbate 80 surfactant [Rote Liste, 1992, Bundesverband der Pharm. Ind. Frankfurt, par. 57020.]

Immediate and sustained release gemfibrozil containing pharmaceutical compositions are disclosed in HU-PS No. 204,192. According to this prior art 0.7–0.8% of polysorbate 80 (Tween 80) is used as surfactant in the preparation of granules.

HU-PS No. 204 194 relates to immediate release gemfibrozil compositions and to compositions from which the active ingredient is delivered in the intestines. Such immediate release granules are prepared by using 0.5% of sodium lauryl sulfate.

HU-PS No. 204,193 relates to water dispersible gemfibrozil containing compositions. These non-sustained release compositions are prepared by first coating the finely distributed gemfibrozil particles with a mixture of a microcrystalline wax and a hydrophilic agent (e.g. fatty alcohols, fatty acid esters, polyols, cellulose derivatives, vinyl derivatives) and thereafter overcoating the particles with 0.5–2.0% of a surfactant. For this purpose as surfactant the use of sodium lauryl sulfate is proposed.

According to the evaluation of prior art in published European patent application No. 462,067, commercially available gemfibrozil capsules contain about 0.2% of sodium lauryl sulfate and tablets commercially available contain about 0.7% of sodium lauryl sulfate. However, this is not sufficient to ensure a suitable dissolution the active ingredient. According to the teachings of European patent application No. 462,067, immediate release gemfibrozil tablets may be prepared by using a larger amount, namely 1–4% relative to the amount of gemfibrozil, of a surfactant having a hydrophilic-lipophilic balance (HLB) between 10 and 50. In the disclosure of said European patent application the following surfactants are enumerated: polysorbates, Pluronic-type additives (polyoxyethylene-polyoxypropylene copolymers), alkali salts of fatty acid sulfates (particularly sodium lauryl sulfate), salts of fatty acids (e.g. sodium oleate) and triethanol amine oleate. It is particularly emphasized in European patent application No. 462,067 that such surfactants must be used in an amount of 1–4% by weight, relative to the gemfibrozil content of the composition.

According to published European patent application No. 475,894, quick dissolution of gemfibrozil tablets can be attained by using buffer salts of strong bases and weak acids as carrier, (e.g. carbonates and citrates) which provide a pH value of above 5 in aqueous medium. It appears, however, from said European patent application that such compositions must contain at least 1% of sodium lauryl sulfate, related to the gemfibrozil content, to achieve the desired quick dissolution the active ingredient.

Surfactants used in orally administered pharmaceutical compositions cannot be regarded to be completely inert auxiliary agents. Namely, such additives do not only promote the dissolution and adsorption of the active ingredient but may also increase the dissolution and adsorption in the gastrointestinal tract of certain other, partly toxic substances. For this reason it is desirable to avoid the use of too high an amount of a surfactant. This is particularly true for pharmaceutical compositions containing active ingredients which are to be administered to the patients in large doses and for a longer period of time because thus a larger amount of surfactant may get into the organism.

Taking into consideration that gemfibrozil belongs to active ingredients which are to be administered in large doses and continuously for a longer period of time, there is a strong demand for gemfibrozil containing pharmaceutical compositions which ensure quick dissolution and adsorption of the active ingredient by using a relatively small amount of a surfactant.

It is therefore an object of the present invention to provide gemfibrozil containing pharmaceutical compositions which eliminate the disadvantages of the known compositions and contain a relatively low amount of a surfactant.

It is a further object of the present invention to eliminate the slowing down of the dissolution of the active ingredient which particularly takes place on storing at a high temperature.

It is a still further object of the present invention to provide gemfibrozil containing solid pharmaceutical compositions showing a small standard deviation in the dissolution velocity of the individual capsules and tablets within a batch and among several batches.

It has been found that the above objects can be achieved in a satisfactory manner by the present invention.

According to the present invention there are provided oral solid pharmaceutical compositions containing as active ingredient gemfibrozil and conventional pharmaceutical auxiliary agents comprising as surfactant bis(2-ethyl-hexyl)-sodium-sulfosuccinate in an amount of 0.05–0.5% by weight, relative to the gemfibrozil content of the composition.

It has been surprisingly found that a relatively small amount (0.05–0.5%, relative to the gemfibrozil content of the composition) of bis-(2-ethyl-hexyl)-sodium-sulfosuccinate (referred to furtheron as "Diotilan") ensures a very quick and uniform dissolution of the active ingredient from tablets or capsules. The standard deviation of dissolution within a given batch and among different batches is very small. A further advantage of the pharmaceutical compositions according to the present invention is that the slowing down of the dissolution velocity, which takes place particularly on longer storing at a high temperature, is efficiently prevented by the addition of Diotilan in the above disclosed amount.

According to a further aspect of the present invention there is provided a process for the preparation of oral solid pharmaceutical compositions containing as active ingredient gemfibrozil and conventional pharmaceutical auxiliary agents which comprises using as surfactant bis-(2-ethylhexyl)-sodium-sulfosuccinate in an amount of 0.05–0.5% by weight, relative to the gemfibrozil content of the composition.

The above advantageous effect of Diotilan used in such a relatively low concentration is unexpected and could not be aforeseen in the light of prior art. According to European patent application No. 462,067, a suitable quick gemfibrozil dissolution can only be achieved by using more than 1% of a hydrophilic surfactant having hydrophilic-lipophilic balance (HLB) between 10 and 50. Diotilan also belongs to the group of surfactants of hydrophilic character. However, European patent application No. 462,067 is completely silent in making any reference to the use of Diotilan.

The gemfibrozil compositions according to the present invention contain Diotilan in addition to conventional auxiliary agents generally used in the manufacture of tablets and capsules. Thus the following auxiliary agents may be preferably used:

filling agents, e.g. microcrystalline cellulose, lactose, mannitol, starch, cellulose or calcium phosphate, etc, binding agents, preferably gelatine, polyvinylpyrrolidone, hydroxypropylmethyl cellulose, polyvinyl alcohol, polyvinyl butyral, etc, disintegrating agents, preferably starch, carboxymethyl starch, carboxymethyl cellulose, cross-linked polyvivinylpyrrolidone, etc, lubricants, preferably magnesium stearate, calcium stearate, stearic acid, hydrogenated castor oil, talc, etc, sliding agents, preferably colloidal silicic acid, talc, etc.

The pharmaceutical compositions of the present invention may be preferably in the form of tablets, film-coated tablets and capsules.

In order to prepare a gemfibrozil containing capsule, tablet or film-coated tablet of the present invention, the active ingredient is homogenized in dry form with 0–40%, by weight of a filling agent (e.g. cellulose, lactose, mannitol, starch, microcrystalline cellulose, calcium phosphate etc.), relative to the capsule filling or the uncoated tablet core. The dry homogenizate may be granuled in a manner known per se, if desired. Granulation may be carried out both by the dry and wet procedures. In case of the "dry procedure" the homogenizate is admixed with not more than 5% by weight of a capsulating tableting binding agent (e.g. polyvinyl pyrrolidone, hydroxypropyl cellulose, polyvinyl butyral, hydroxypropylmethyl cellulose, gelatine etc.) and 0.05–0.5% by weight of Diotilan, relative to the amount of gemfibrozil, the mixture is converted into briquettes by pressing, or transformed into tablets, ground and sieved to the desired particle size (e.g. 0.1–1.0 mm). "Wet granulation" may be performed by kneading the homogenizate with a solution of not more than 5% by weight of a capsulating tableting binding agent (e.g. polyvinyl pyrrolidone, hydroxypropylmethyl cellulose, gelatine, polyvinyl alcohol etc.) and 0.05–0.5% by weight of Diotilan, relative to the amount of gemfibrozil, formed with water or a $C_{1-3}$ alkanol or a mixture of water and alkanol. One may also proceed by spraying the solution of the binding agent and Diotilan onto the powder mixture fluidized in a fluidization-type granulating apparatus. The granules thus obtained are dried and sieved to the desired particle size (generally below 1.0 mm). The homogenizate or the granules prepared therefrom are then admixed with lubricant (e.g. magnesium stearate, calcium stearate, stearic acid, hydrogenated castor oil or talc) and/or a sliding agent (e.g. colloidal silicic acid or talc), capsuled or tabletted, whereby the tablets may be film-coated by using water soluble polymers (e.g. hydroxypropylmethyl cellulose, polyethylene glycol etc.), if desired.

The quality of the composition may be characterized by the uniformity of the dissolution of the active ingredient and the uniformity of dissolution velocity. The gemfibrozil dissolution of the compositions is determined with the aid of the "paddle" method, disclosed in USP XXII, at 37° C. using 900 ml of a phosphate buffer (pH 7.4) as dissolving medium. The amount of the released gemfibrozil is determined by means of HPLC.

The amount of gemfibrozil released from the compositions is determined immediately, at the beginning of the dissolution test, and after 5, 15, 30 and 45 minutes, respectively. Six replicates were used for each batch (capsules, film-coated tablets, tablets) and the average percentage amount of gemfibrozil dissolved from each tablet or the average percentage amount of gemfibrozil dissolved from six compositions is graphically plotted.

The uniformity is of dissolution characterized by calculating at a given point of time the relative standard deviation (rsd) of the percentage amount of dissolved gemfibrozil within one single batch, the average value of the dissolution from 6 tablets each and the standard deviation of the average values among the different batches (RSD). These values are shown in diagrams and compared with the dissolution data. rsd and RSD values of commercially available gemfibrozil containing solid pharmaceutical compositions.

The rsd and RSD values are calculated on the basis of the following equations:

$$\text{Average } (X) = \frac{\Sigma x}{n}$$

$$\text{Deviation } (s) = \frac{n * \Sigma x^2 - (\Sigma x)^2}{n}$$

$$rsd = \frac{s}{X} * 100$$

-continued $$\text{Deviation of average values } (S) = \frac{N^*\Sigma x^2 - (\Sigma x)^2}{N}$$

$$RSD = \frac{S^*N}{X} * 100$$

wherein x=measured dissolution values (%), n=number of parallel measurements (replicates, 6 for each batch), X=average dissolution value (per batch), N=number of tested batches, s=standard deviation of dissolution values (within one batch), S=standard deviation of dissolution values (among the different batches), rsd=percentage standard deviation (within one batch), RSD=percentage standard deviation (among the different batches).

Further details of the present invention are to be found in the following Examples without limiting the scope of protection to said Examples.

EXAMPLE 1

Gemfibrozil Capsule

Gemfibrozil capsules having the following composition are prepared:

| Component | Amount, mg/capsule |
| --- | --- |
| Gemfibrozil | 300 |
| Maize starch | 63 |
| Hydroxypropylmethyl cellulose | 16 |
| Magnesium stearate | 6 |
| Sodium carboxymethyl starch | 12 |
| Colloidal silicic acid | 2.4 |
| Diotilan | 0.4 |

The gemfibrozil and maize starch are homogenized in a Lödige mixer and thereafter granulated with the aqueous solution of Diotilan and hydroxypropylmethyl cellulose. The granules are dried, screened over a 0.8 mm sieve screen, returned into the Lödige apparatus, whereupon the components of the external layer (magnesium stearate, sodium carboxymethyl starch, colloidal silicic acid) are added and the mixture is homogenized. The homogenized mixture is then filled into hard gelatine capsules, size "0".

The release of the active ingredient (dissolution) is determined according to the "paddle" method disclosed in USP XXII, at 37° C., using 900 ml of a phosphate buffer (pH 7.4) as dissolving medium. The amount of the released gemfibrozil is determined by HPLC.

Figure 1:
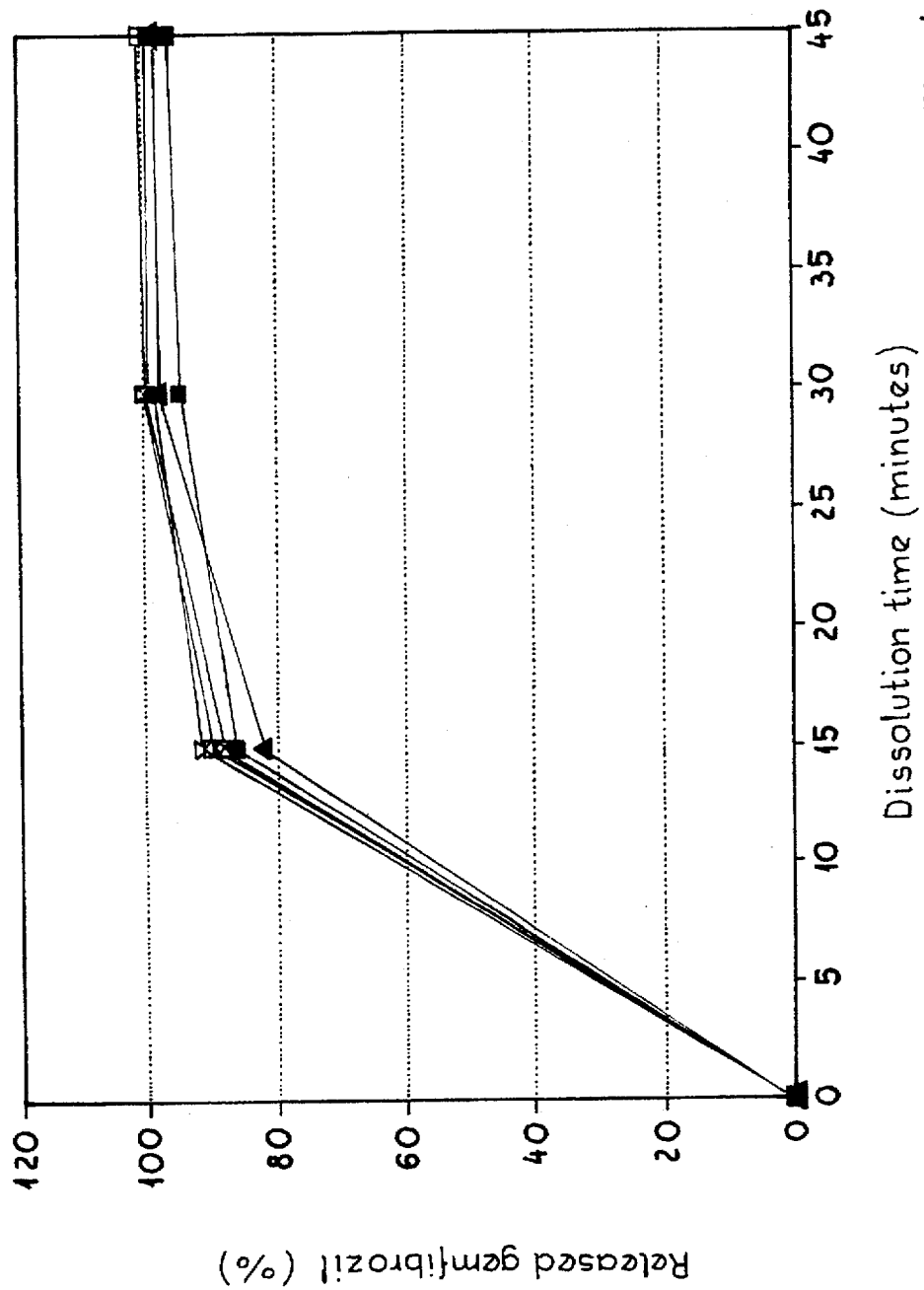
FIG. 1 is a graph of the rate of dissolution as a function of Released gemfibrozil (%) versus Dissolution time (minutes) for 6 capsules of the claimed gemfibrozil composition.
Figure 2:
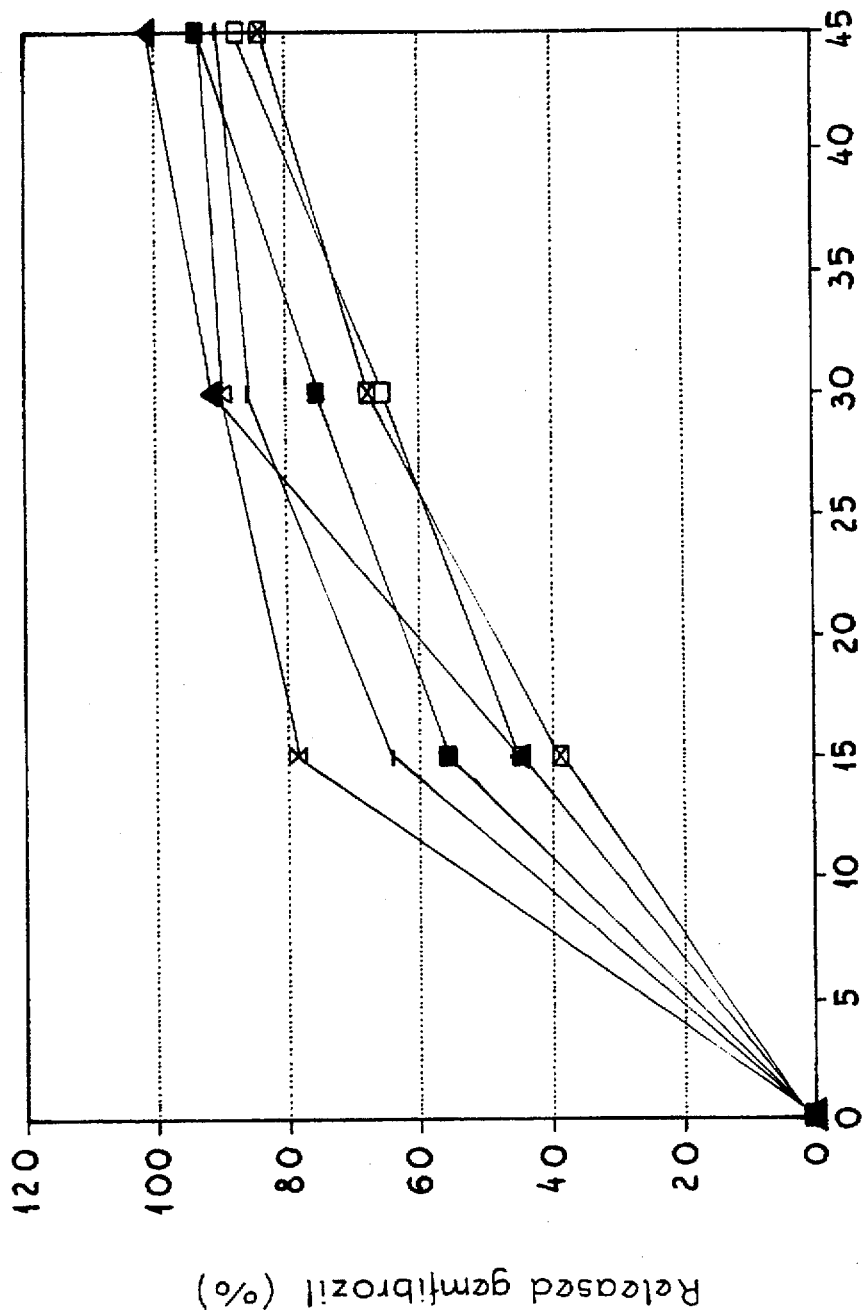
FIG. 2 is a graph of the rate of dissolution as a function of Released gemfibrozil (%) versus Dissolution time (minutes) for 6 commercially-available capsules.

The dissolution data of the capsules prepared according to the present invention are disclosed and compared with those of commercially available (USA) capsules in FIG. 1 (capsules of the present invention) and FIG. 2 (commercially available capsules).

Figure 3:
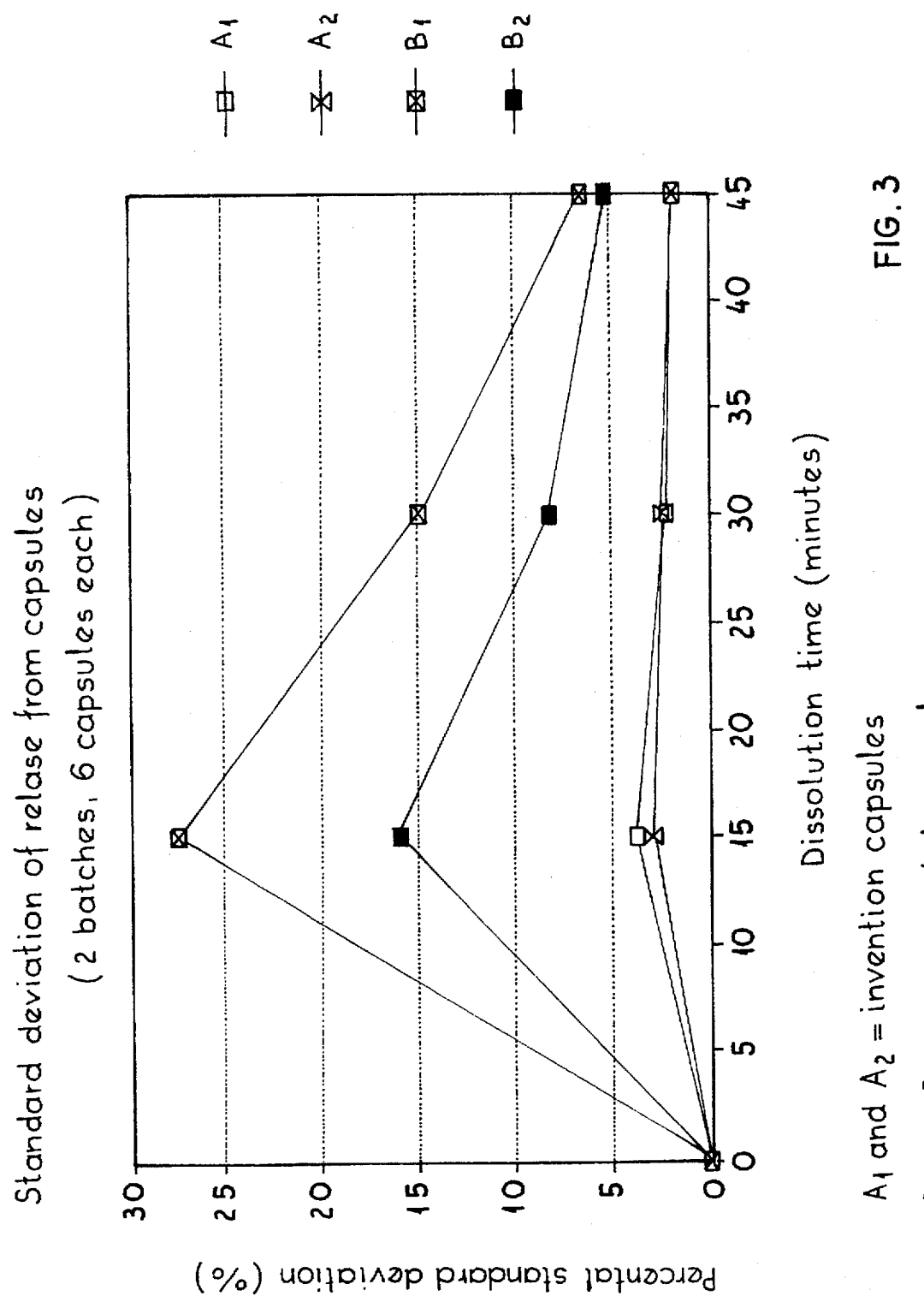
FIG. 3 is a graph that compares the variability of gemfibrozil release as a function of time of capsules of the claimed gemfibrozil composition with commercially-available capsules.

The standard deviation of each batch (6 capsules were used for the dissolution test) is calculated from the experimental data. The time dependence of the rsd values is shown in FIG. 3.

It appears from the above data that the active ingredient dissolution within one batch is more uniform (smaller standard deviation) in case of the invention capsules than by the commercially available reference capsules.

EXAMPLE 2

Gemfibrozil Film-coated Tablets

Gemfibrozil containing film-coated tablets having the following composition are prepared:

| Component | Amount, mg/capsule |
| --- | --- |
| Gemfibrozil | 600.0 |
| Microcrystalline cellulose | 120.0 |
| Gelatine | 40.0 |
| Diotilan | 2.0 |
| Calcium stearate | 16.0 |
| Sodium carboxymethyl starch | 54.0 |
| Talc | 24.0 |
| Colloidal silicic acid | 8.0 |

| Film-coating | Amount, mg |
| --- | --- |
| Hydroxypropylmethyl cellulose | 9.5 |
| Polyethyleneglycol | 4.0 |
| Simethicone | 0.5 |
| Titanium dioxide | 2.0 |
| Total weight: | 880.0 mg. |

The gemfibrozil and microcrystalline cellulose are homogenized in a Lödige whirlpool mixer and the homogenizate is granuled with a mixture of the aqueous solution of gelatine (pH 3–4) and the ethanolic solution of Diotilan. The granules are dried, screened through a 0.8 mm sieve screen, returned into the Lödige mixer and homogenized with the components of the external layer (calcium stearate, sodium carboxymethyl starch, talc, colloidal silicic acid). The homogenized mixture is pressed into oval biconvex tablets weighing 864 mg. The tablets are coated in a dragée vessel with a water soluble film by spraying onto the tablets an aqueous dispersion of the above coating components.

The dissolution of the active ingredient is determined by the method described in USP XXII by the "paddle" method, at 37° C., by using 900 ml of a phosphate buffer (pH 7.4) as dissolving medium. The amount of the released gemfibrozil is measured by HPLC.

The dissolution data of the film-coated tablets according to the present invention and those of commercially available (US) film-coated tablets are determined immediately after manufacture and purchase, respectively, and also after storing at 40° C. for 3 months. For both the invention and purchased film-coated tablets 3 batches were used each for the test and each batch consisted of 6 film-coated tablets.

Figure 4:
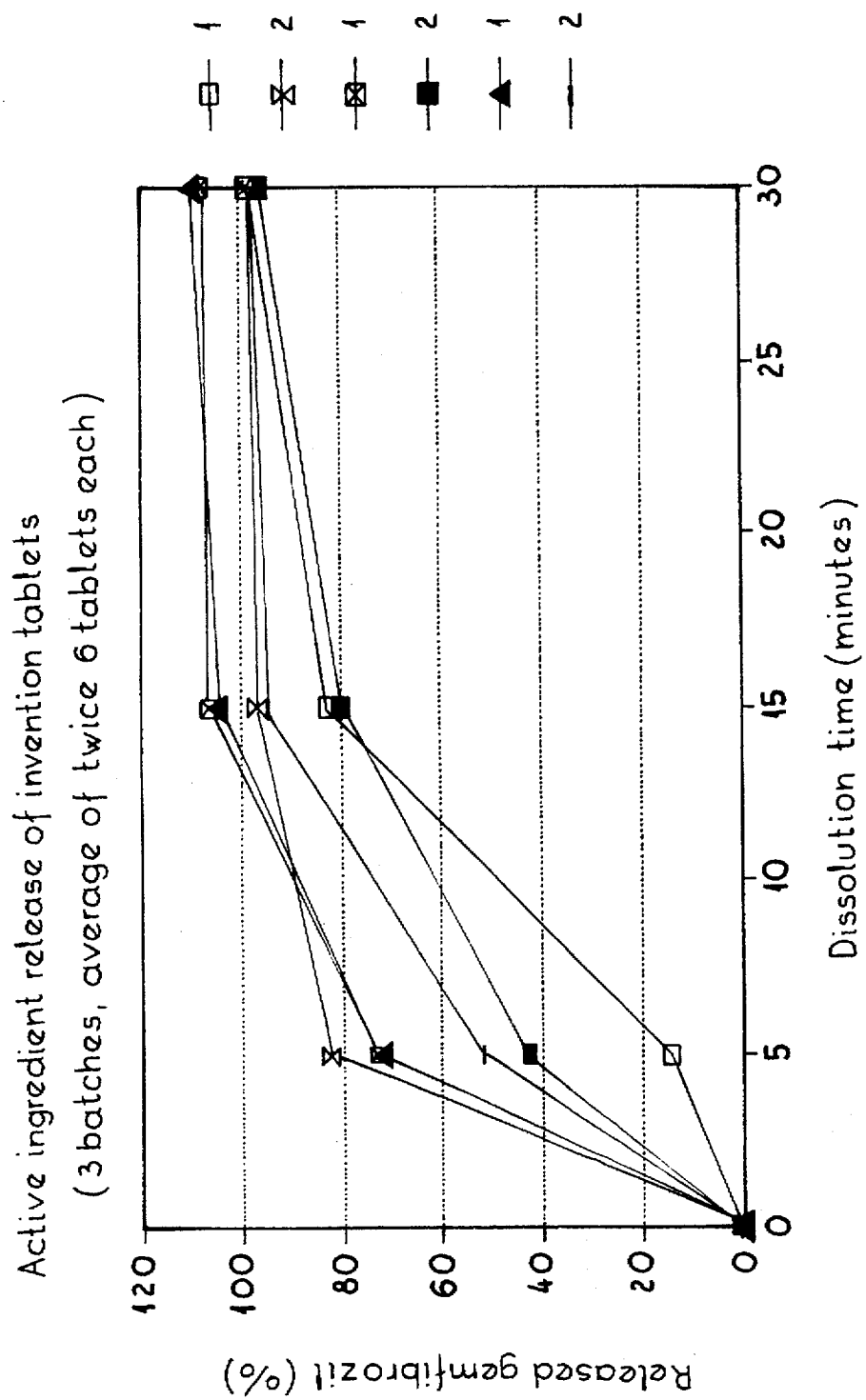
FIG. 4 is a graph of a comparison of release rates of gemfibrozil of three batches of film-coated tablets made from the claimed gemfibrozil composition measured after manufacture and after storage at 40° C. for 3 months.
Figure 5:
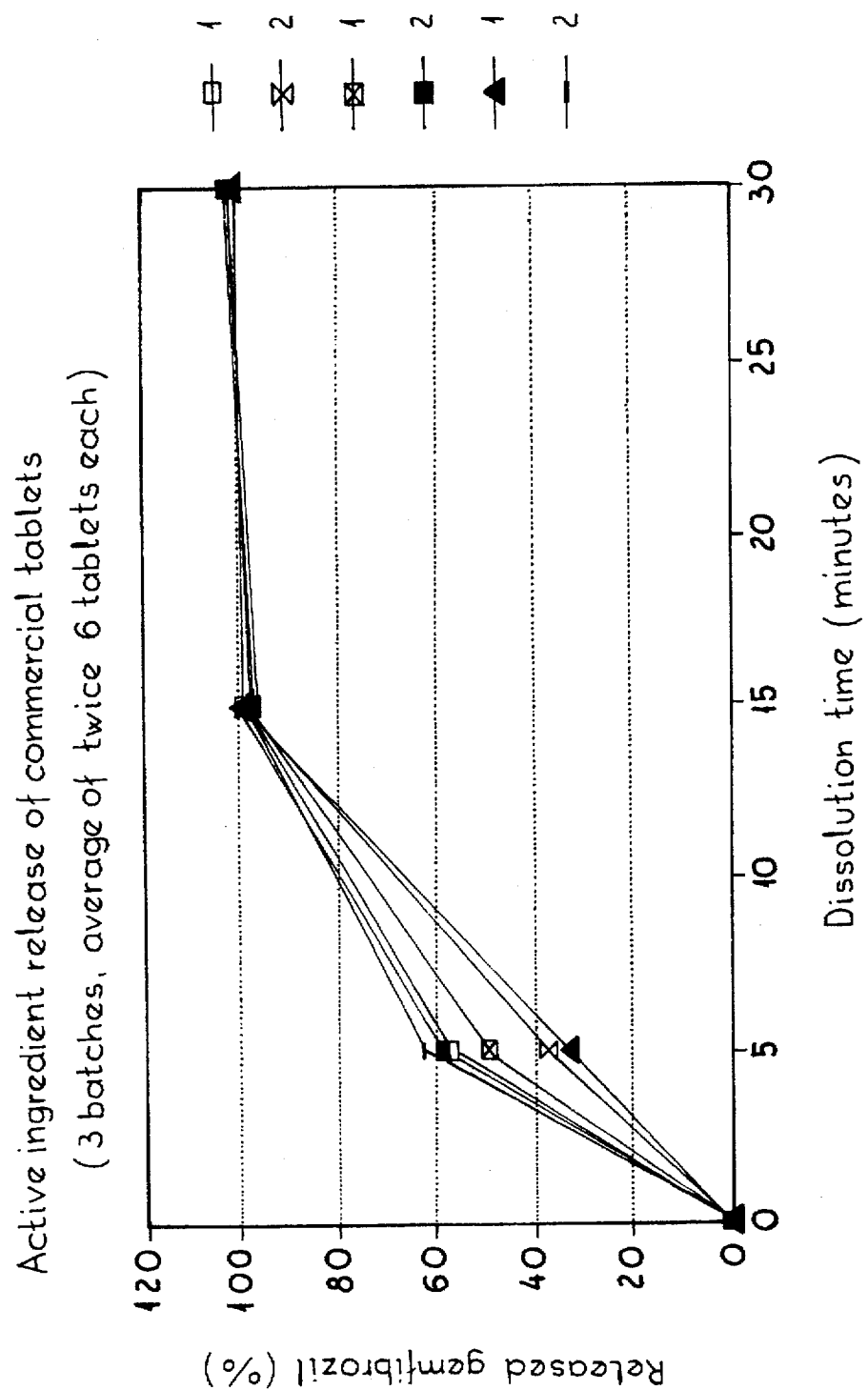
FIG. 5 is a graph of a comparison of release rates of gemfibrozil of three batches of commercially-available film-coated tablets measured after purchase and after storage at 40° C. for 3 months.

In FIG. 4 in case of the composition according to the present invention data obtained for 3 batches consisting of 6 tablets each are presented. Average data obtained immediately after manufacture and after storing at 40° C. for 3 months, respectively, are shown. FIG. 5 displays the corresponding data obtained for 3 batches of the commercially available composition.

The diagrams clearly show that the dissolution velocity from the commercially available film-coated tablets significantly decrease after storing. Moreover, in commercially available samples the average values of dissolution measured in various batches show a much higher standard deviation than those obtained for the invention compositions.

In order to characterize the uniform dissolution more precisely the relative standard deviation (RSD) of the average values of the individual batches for the invention and commercially available film-coated tablets were calculated and the values obtained are plotted against the time. The results are shown in FIG. 6.

Figure 6:
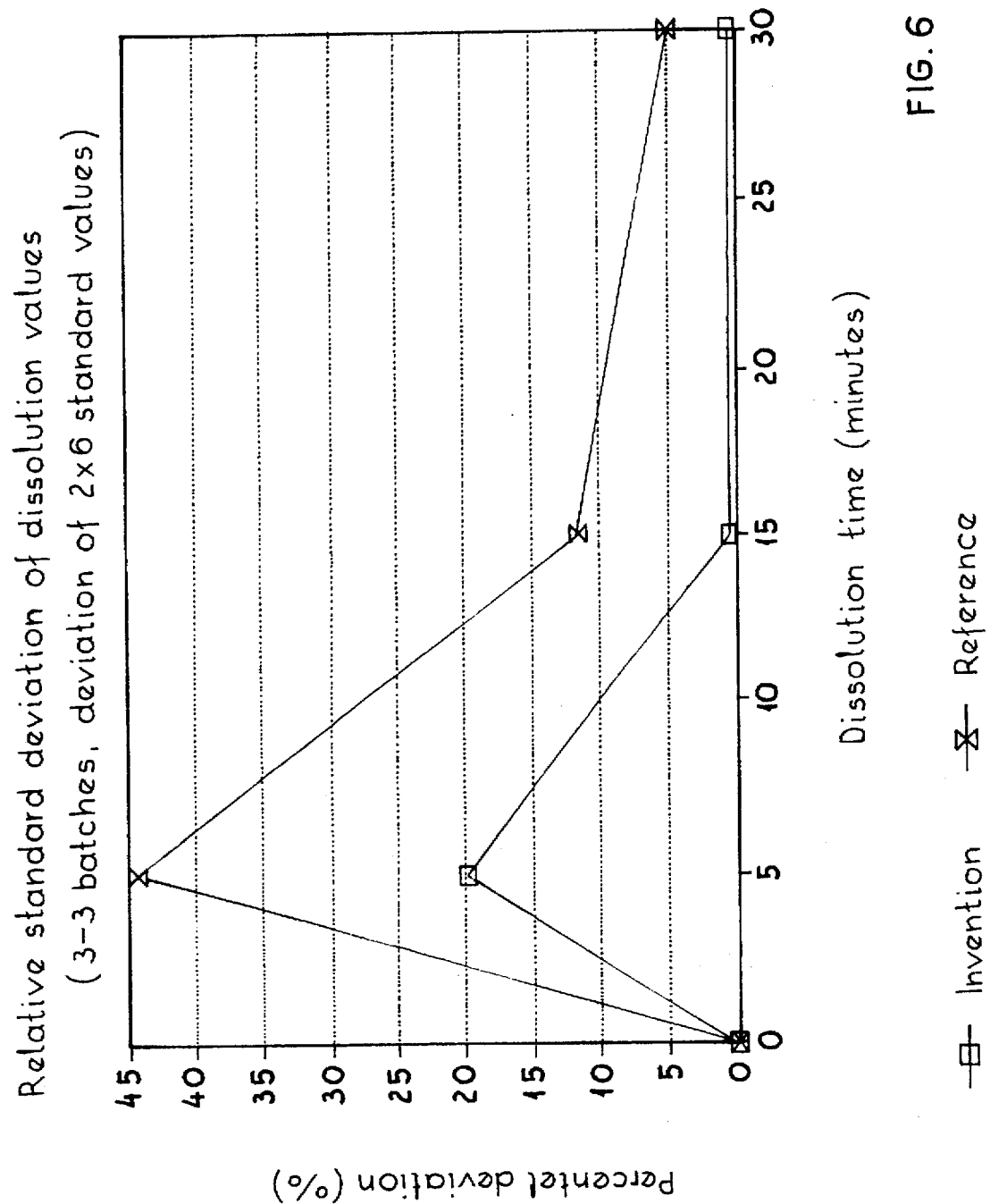
FIG. 6 is a graph that compares the variability of gemfibrozil release as a function of time of film-coated tablets of the claimed gemfibrozil composition with commercially available film-coated tablets.

It can be seen from FIG. 6 that the standard deviation of the dissolution among the individual batches is significantly lower in case of the product according to the present invention than by the commercially available reference product.

EXAMPLE 3

Comparative Test

The dissolution velocity of Diotilan containing tablets according to the present invention, tablets containing identical amount of sodium lauryl sulfate and tablets containing no surfactant is determined and compared.

Tablets are prepared according to Example 2 (Experiment 3A). According to Experiment 3B Diotilan is replaced by the same amount of sodium lauryl sulfate. According to Experiment 3C no surfactant is added to the granulating solution. In Experiments 3A and 3B the weight of the tablets amounts to 864 mg and in Experiment 3C to 862 mg.

The dissolution of the tablets is measured as described in Example 2 except that no film-coating is applied.

The dissolution results are summarized in the following Table.

| Time of dissolution | Experiment 3A 0.33% of Diotilan | Experiment 3B 0.33% of sodium lauryl sulfate | Experiment 3C No surfactant |
| --- | --- | --- | --- |
| 5 minutes  | 80%  | 36%  | 14%  |
| 15 minutes | 100% | 81%  | 39%  |
| 30 minutes | 100% | 100% | 64%  |
| 45 minutes | 100% | 100% | 81%  |
| 60 minutes |      |      | 90%  |
| 75 minutes |      |      | 100% |

The above data clearly demonstrate that in the absence of a surfactant the dissolution velocity is very low. A 33% amount of sodium lauryl sulfate results in an increase of dissolution velocity but the results obtained with Diotilan according to the present invention give much better results. It is surprising that Diotilan in the low concentration used provides such a quick release and dissolution of the gemfibrozil active ingredient.

We claim:

1. Oral solid pharmaceutical composition containing as active ingredient gemfibrozil and conventional pharmaceutical auxiliary agents comprising as surfactant bis-(2-ethyl-hexyl)-sodium-sulfosuccinate in an amount of 0.05–0.5% by weight, relative to the gemfibrozil content of the composition.

2. Pharmaceutical composition according to claim 1 wherein the amount of bis-(2-ethyl-hexyl)-sodium-sulfosuccinate content is 0.1–0.4% by weight of the gemfibrozil of the composition.

3. Pharmaceutical composition according to claim 1 wherein said auxiliary agent is a filler selected from the group consisting of microcrystalline cellulose, lactose, mannitol, starch, cellulose and calcium phosphate.

4. Pharmaceutical composition according to claim 1 wherein said auxiliary agent is a binding agent selected from the group consisting of gelatine, polyvinyl pyrrolidone, hydroxypropyl-methyl cellulose, polyvinyl alcohol and polyvinyl butyral.

5. Pharmaceutical composition according to claim 1 wherein said auxiliary agent is a disintegrating agent selected from the group consisting of starch, carboxymethyl starch, carboxymethyl cellulose and cross-linked polyvinyl pyrrolidone.

6. Pharmaceutical composition according to claim 1 wherein said auxiliary agent is a lubricant selected from the group consisting of magnesium stearate, calcium stearate, steric acid, hydrogenated castor oil and talc.

7. Pharmaceutical composition according to claim 1 wherein said auxiliary agent is a sliding agent selected from the group consisting of colloidal silicic acid and talc.

8. Pharmaceutical composition according to claim 1 in the form of capsules, tablets or film-coated tablets.

9. Process for the preparation of oral solid pharmaceutical compositions containing as active ingredient gemfibrozil and conventional pharmaceutical auxiliary agents which comprises mixing gemfibrozil and bis-(2-ethyl-hexyl)-sodium-sulfosuccinate as surfactant in an amount of 0.05–0.5% by weight, relative to the gemfibrozil content of the composition.

10. Process according to claim 9 which comprises mixing gemfibrozil and bis-(2-ethyl-hexyl)-sodium-sulfosuccinate as surfactant in an amount of 0.1–0.4% by weight, relative to the gemfibrozil content of the composition.

11. Pharmaceutical composition according to claim 2 wherein said auxiliary agent is a filler selected from the group consisting of microcrystalline cellulose, lactose, mannitol, starch, cellulose and calcium phosphate.

12. Pharmaceutical composition according to claim 2 wherein said auxiliary agent is a binding agent selected from the group consisting of gelatine, polyvinyl pyrrolidone, hydroxypropyl-methyl cellulose, polyvinyl alcohol and polyvinyl butyral.

13. Pharmaceutical composition according to claim 2 wherein said auxiliary agent is a disintegrating agent selected from the group consisting of starch, carboxymethyl starch, carboxymethyl cellulose and cross-linked polyvinyl pyrrolidone.

14. Pharmaceutical composition according to claim 2 wherein said auxiliary agent is a lubricant selected from the group consisting of magnesium stearate, calcium stearate, steric acid, hydrogenated castor oil and talc.

15. Pharmaceutical composition according to claim 2 wherein said auxiliary agent is a sliding agent selected from the group consisting of colloidal silicic acid and talc.

16. Pharmaceutical composition according claim 2 in the form of capsules, tablets or film-coated tablets.

17. Pharmaceutical composition according claim 3 in the form of capsules, tablets or film-coated tablets.

18. Pharmaceutical composition according claim 4 in the form of capsules, tablets or film-coated tablets.

19. Pharmaceutical composition according claim 5 in the form of capsules, tablets or film-coated tablets.

20. Pharmaceutical composition according claim 6 in the form of capsules, tablets or film-coated tablets.

* * * * *